(12) United States Patent
Anderson et al.

(10) Patent No.: US 10,899,924 B2
(45) Date of Patent: Jan. 26, 2021

(54) AQUEOUS BINDER COMPRISING REACTION PRODUCTS OF ITACONIC ACID

(71) Applicant: CARGILL, INCORPORATED, Wayzata, MN (US)

(72) Inventors: Kevin R. Anderson, Cedar Rapids, IA (US); Ryan L. Flynn, Minneapolis, MN (US); Frank P. Lochel, Rock Hill, SC (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 16/725,008

(22) Filed: Dec. 23, 2019

(65) Prior Publication Data

US 2020/0140681 A1 May 7, 2020

Related U.S. Application Data

(63) Continuation of application No. 15/742,125, filed as application No. PCT/US2016/041253 on Jul. 7, 2016, now Pat. No. 10,544,300.

(60) Provisional application No. 62/189,613, filed on Jul. 7, 2015.

(51) Int. Cl.
| | | |
|---|---|---|
| C08L 67/02 | (2006.01) | |
| C08K 5/00 | (2006.01) | |
| D06M 15/51 | (2006.01) | |
| E04B 1/74 | (2006.01) | |
| B01J 23/745 | (2006.01) | |
| B01J 27/053 | (2006.01) | |
| C07C 57/13 | (2006.01) | |
| C03C 25/323 | (2018.01) | |
| C09K 3/22 | (2006.01) | |
| C08G 63/52 | (2006.01) | |
| C08K 5/092 | (2006.01) | |
| D04H 1/587 | (2012.01) | |
| C08J 5/04 | (2006.01) | |
| C08K 5/05 | (2006.01) | |
| D04H 1/4218 | (2012.01) | |
| D04H 1/64 | (2012.01) | |
| E04B 1/78 | (2006.01) | |

(52) U.S. Cl.
CPC ............ *C08L 67/02* (2013.01); *C03C 25/323* (2013.01); *C08G 63/52* (2013.01); *C08J 5/043* (2013.01); *C08K 5/0025* (2013.01); *C08K 5/05* (2013.01); *C08K 5/092* (2013.01); *C09K 3/22* (2013.01); *D04H 1/4218* (2013.01); *D04H 1/587* (2013.01); *D04H 1/64* (2013.01); *D06M 15/51* (2013.01); *E04B 1/74* (2013.01); *B01J 23/745* (2013.01); *B01J 27/053* (2013.01); *C07C 57/13* (2013.01); *C08J 2367/06* (2013.01); *E04B 1/78* (2013.01)

(58) Field of Classification Search
CPC ...... C08L 67/02; C08K 5/0025; D06M 15/51; E04B 1/74; C07C 57/13; B01J 27/053; B01J 23/745
See application file for complete search history.

(56) References Cited

U.S. PATENT DOCUMENTS

| | | |
|---|---|---|
| 5,223,592 A | 6/1993 | Hughes et al. |
| 6,699,945 B1 | 3/2004 | Chen et al. |
| 8,053,528 B2 | 11/2011 | Shoemake et al. |
| 8,901,223 B2 | 12/2014 | Anderle et al. |
| 2013/0248753 A1 | 9/2013 | Lai et al. |
| 2014/0038485 A1 | 2/2014 | Anderson et al. |
| 2014/0051824 A1 | 2/2014 | Anderson et al. |

OTHER PUBLICATIONS

Stawski, et al., "Polymerization of itaconic acid", Polimery 2005, 50, nr 2, pp. 118-122.

*Primary Examiner* — Shane Fang

(57) ABSTRACT

An aqueous binder composition is provided for use in the formation of fiber insulation and non-woven mats that comprises a reaction product of one or more Liquid Polyol Monomers; itaconic acid, its salts or anhydride; and a C4 to C6 polyol selected from the group consisting of pentaerythritol, trimethylol propane, neopentyl glycol, and mixtures thereof. The molar ratio of the combined alcohols (Liquid Polyol Monomers and C4 to C6 polyols) to itaconic acid is at least 2:1, wherein the molar ratio of Liquid Polyol Monomers to C4 to C6 polyols is from about 1:1 to about 30:1.

21 Claims, No Drawings

AQUEOUS BINDER COMPRISING REACTION PRODUCTS OF ITACONIC ACID

CROSS-REFERENCE TO RELATED APPLICATIONS

This application is continuation of U.S. patent application Ser. No. 15/742,125, filed Jan. 5, 2018, entitled AQUEOUS BINDER COMPRISING REACTION PRODUCTS OF ITACONIC ACID, a national phase application of international application PCT/US2016/04125, filed Jul. 7, 2016, and entitled AQUEOUS BINDER COMPRISING REACTION PRODUCTS OF ITACONIC ACID, which claims the benefit of U.S. Provisional Patent Application No. 61/189,613, filed Jul. 7, 2015, entitled AQUEOUS BINDER. COMPRISING REACTION PRODUCTS OF ITACONIC ACID, both of which are hereby incorporated by reference in their entirety.

FIELD OF THE INVENTION

The present invention relates to aqueous binder compositions. More specifically, the present invention relates to aqueous binder compositions for use in the formation of insulation and non-woven mats.

BACKGROUND OF THE INVENTION

Conventional fibers are useful in a variety of applications including reinforcements, textiles, and acoustical and thermal insulation materials. Although mineral fibers (e.g., glass fibers) are typically used in insulation products and non-woven mats, depending on the particular application, organic fibers such as polypropylene, polyester, and multi-component fibers may be used alone or in combination with mineral fibers in forming the insulation product or non-woven mat.

Certain fibrous insulation is typically manufactured by fiberizing a molten composition of polymer, glass, or other mineral and spinning fine fibers from a fiberizing apparatus, such as a rotating spinner. To form an insulation product, fibers produced by the rotating spinner are drawn downwardly from the spinner towards a conveyor by a blower. As the fibers move downward, a binder material is sprayed onto the fibers and the fibers are collected into a high loft, continuous blanket on the conveyor. The binder material gives the insulation product resiliency for recovery after packaging and provides stiffness and handleability so that the insulation product can be handled and applied as needed in the insulation cavities of buildings. The binder composition also provides protection to the fibers from interfilament abrasion and promotes compatibility between the individual fibers.

The blanket containing the binder-coated fibers is then passed through a curing oven and the binder is cured to set the blanket to a desired thickness. After the binder has cured, the fiber insulation may be cut into lengths to form individual insulation products, and the insulation products may be packaged for shipping to customer locations. One typical insulation product produced is an insulation batt or blanket, which is suitable for use as wall insulation in residential dwellings or as insulation in the attic and floor insulation cavities in buildings.

Non-woven mats may be formed by conventional wet-laid processes. For example, wet chopped fibers are dispersed in a water slurry that contains surfactants, viscosity modifiers, defoaming agents, and/or other chemical agents. The slurry containing the chopped fibers is then agitated so that the fibers become dispersed throughout the slurry. The slurry containing the fibers is deposited onto a moving screen where a substantial portion of the water is removed to form a web. A binder is then applied, and the resulting mat is dried to remove any remaining water and cure the binder. The formed non-woven mat is an assembly of dispersed, individual glass filaments.

Various attempts have been made to reduce undesirable formaldehyde emissions from formaldehyde-based resins. For example, various formaldehyde scavengers such as ammonia and urea have been added to the formaldehyde-based resin in an attempt to reduce formaldehyde emission from the insulation product. Because of its low cost, urea is added directly to the uncured resin system to act as a formaldehyde scavenger. The addition of urea to the resin system produces urea-extended phenol-formaldehyde resole resins. These resole resins can be further treated or applied as a coating or binder and then cured. Unfortunately, the urea-extended resoles are unstable, and because of this instability, the urea-extended resoles must be prepared on site. In addition, the binder inventory must be carefully monitored to avoid processing problems caused by undesired crystalline precipitates of dimer species that may form during storage. Ammonia is not a particularly desirable alternative to urea as a formaldehyde scavenger because ammonia generates an unpleasant odor and may cause throat and nose irritation to workers. Further, the use of a formaldehyde scavenger in general is undesirable due to its potential adverse affects to the properties of the insulation product, such as lower recovery and lower stiffness.

In addition, previous arts have focused on the use of polyacrylic acid with a polyhydroxy crosslinking agent or carbohydrate-based chemistry that is linked to the Maillard reaction. A binder that is formed mostly of polyacrylic acid inherently has problems due to its acidity and associated corrosion of machine parts. In addition, polyacrylic acid binders have a high viscosity, high curing temperatures, and high associated curing costs. Further, the Maillard-based products have an undesirable dark brown color after curing. Also, the use of large amounts of ammonia needed to make the binder presents a safety risk and possible emission problems.

Alternative polymeric binder systems to those described above for fibrous glass products have also been proposed. However, these alternative binder systems remain problematic. For example, low molecular weight, low viscosity binders which allow maximum vertical expansion of the insulation pack in the transfer zone generally cure to form a non-rigid plastic matrix in the finished product, thereby reducing the attainable vertical height recovery of the finished insulation product when installed. Conversely, high viscosity binders, which generally cure to form a rigid matrix in the finished product, do not allow the desired maximum vertical expansion of the coated, uncured pack.

US Published Patent Application No. 2013/0248753 to Lai describes polymers comprising structural units derived from itaconic acid which are useful as binders for fiberglass. The polymer is stated to be a homopolymer or a copolymer that may be grafted with one or more polyols. See paragraph [0006]. The polyols that may be grafted to the polymer backbone are described, for example, at paragraph [0011], which in particular states that it is preferred that at least 50 wt. % of the polyols are glycerol. Paragraph [0012] states that the number of structural units derived from itaconic acid, or anhydride or salt thereof, and/or the one or more co-monomers in the polymer backbone that may be grafted with a polyol may be up to about 30% of the structural units.

US Published Patent Application No. 2014/0051824 to Anderson describes a pre-reacted product of a polyol and monomeric or polymeric polycarboxylic acid or polyglycerol, which when used in a binder, helps to speed the crosslinking reaction, induces faster water evaporation, decreases the viscosity of the binder, helps to reduce the amount of water needed for application of the binder, and decreases tackiness. The pre-reacted product may be used, for example, in the formation of insulation materials and non-woven chopped strand mats. See the Abstract. The acid described for use in preparation of this reaction product is citric acid, which is a saturated tricarboxylic acid compound. US Published Patent Application No. 2014/0038485 to Anderson describes an aqueous binder composition that includes a carbohydrate, a crosslinking agent, and a pre-reacted product of an alcohol or polyol and monomeric or polymeric polycarboxylic acid or polyglycerol. The pre-reacted product is similar to that described in US Published Patent Application No. 2014/0051824, which is incorporated by reference at paragraph [0057]. The binder is cured and cross-linked by a condensation reaction to form a polyester.

SUMMARY OF THE INVENTION

An aqueous binder compositions are provided that comprise water and a reaction product of one or more Liquid Polyol Monomers (i.e. polyol monomer compounds having a melting point below 23° C. (73° F.)); itaconic acid; and a C4 to C6 polyol selected from the group consisting of pentaerythritol, trimethylol propane, neopentyl glycol, and mixtures thereof. The molar ratio of the combined alcohols (Liquid Polyol Monomers and C4 to C6 polyols) to itaconic acid is at least 2:1. In an embodiment, the molar ratio of the combined alcohols (Liquid Polyol Monomers and C4 to C6 polyols) to itaconic acid is at least about 2:1, wherein the molar ratio of Liquid Polyol Monomers to C4 to C6 polyols is from about 1:1 to about 30:1. In an embodiment, the molar ratio of the combined alcohols (Liquid Polyol Monomers and C4 to C6 polyols) to itaconic acid is from about 2:1 to about 5:1, wherein the molar ratio of Liquid Polyol Monomers to C4 to C6 polyols is from about 1:1 to about 30:1. For purposes of the present description, unless otherwise stated references to itaconic acid include itaconic acid salts and/or itaconic acid anhydride.

The reaction product comprises a vinyl functionality that is readily available for reaction to form a binder. The use of both Liquid Polyol Monomers and C4 to C6 polyols in the manner described herein as reaction components provides a reaction product that exhibits a unique balance of water compatibility properties, so that the reaction product is stable in aqueous binder formulations while at the same time is readily formulated in a binder composition from which water may be efficiently removed. This balance of properties provides exceptional benefit particularly in the manufacturing process for formation of fiber insulation and non-woven mats. In particular, aqueous binders of the present invention permit faster processing in manufacture of nonwoven products because they induce faster water evaporation, have low binder viscosity, and reduce the amount of water needed for application of the binder.

Binders comprising the reaction product as described herein may be formulated with materials that are environmentally friendlier, less toxic and less acidic/corrosive than conventional binders used for formation of fiber insulation and non-woven mats. Additionally, the materials used for preparation of the reaction product may be inexpensively acquired and may be obtained from bio-based sources.

Further, the present selection of alcohols for reaction with itaconic acid provides a binder component that has a desirably high smoke point, while still being liquid. It has been discovered that binder components comprising only glycerol as the alcohol reactant have an undesirably low smoke point, while binder components comprising only pentaerythritol as the alcohol reactant are solid, and therefore difficult to formulate in a liquid binder composition.

Because the present reaction product is made using itaconic acid, the resulting product comprises a double bond that has been found to be readily available for efficient addition reaction in formation of an effective binder, with or without incorporation of other addition polymerizable materials. Further, the reaction of the binder composition polymer via the double bond functionality provides a non-reversible cure of the binder, in contrast with a reversible cure of other binder compositions.

Aqueous binder compositions described herein are preferably used in the formation of fiber insulation and non-woven mats. In embodiments of the present invention, the aqueous binder compositions may be used in formation of sand molds, for example in casting operations, and used in fiberboard construction and other such applications where fibers and/or particles are adhered to surfaces or to other fibers and/or particles. For sand molds and other high mass, thick articles of manufacture, additional heat may be applied to the interior of the article of manufacture to speed the curing reaction of the binder composition. Examples of methods for applying heat to the interior of the article of manufacture include adding material to the binder composition that reacts exothermically once a reaction is initiated.

DETAILED DESCRIPTION OF PRESENTLY PREFERRED EMBODIMENTS

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

The reaction product described herein for use in an aqueous binder composition is the reaction product of selected alcohols (i.e. Liquid Polyol Monomers and C4 to C6 polyols) with itaconic acid, itaconic acid salt or itaconic acid anhydride. The selection of itaconic acid in combination with certain alcohols as described herein provides a unique binder composition.

Itaconic acid may, for example, be obtained by the distillation of citric acid or by the fermentation of carbohydrates such as glucose using, for example, *Aspergillus terreus*. Itaconic acid may be referred to as methylenesuccinic acid or 2-methylidenebutanedioic acid. The salts used with itaconic acid may include sodium, potassium or ammonium salts of itaconic acid. The salts may include alkylated ammonium salts such as triethyl ammonium salt, and hydroxyl alkylated ammonium salts such as triethanol ammonium salt, and the like.

In an embodiment, one of the alcohols to be reacted with itaconic acid is selected from one or more Liquid Polyol Monomers selected from the group consisting of glycerol, propylene glycol, ethylene glycol, diglycerol, dipropylene glycol, diethylene glycol and mixtures thereof. In an embodiment of the present invention, the Liquid Polyol Monomers comprises glycerol. In an embodiment, at least about 90% by weight of the Liquid Polyol Monomers used in preparation of the reaction product is glycerol. In an embodiment of the present invention, the Liquid Polyol Monomers comprises propylene glycol. In an embodiment, at least about 90% by weight of the Liquid Polyol Monomers used in preparation of the reaction product is propylene glycol. In an embodiment of the present invention, the Liquid Polyol Monomers comprises ethylene glycol. In an embodiment, at least about 90% by weight of the Liquid Polyol Monomers used in preparation of the reaction product is ethylene glycol. In an embodiment, at least about 90% by weight of the Liquid Polyol Monomers used in preparation of the reaction product is a mixture of glycerol and propylene glycol. In an embodiment, at least about 90% by weight of the Liquid Polyol Monomers used in preparation of the reaction product is a mixture of glycerol and ethylene glycol. In an embodiment, at least about 90% by weight of the Liquid Polyol Monomers used in preparation of the reaction product is a mixture of propylene glycol and ethylene glycol.

The other of the alcohol to be reacted with itaconic acid is a C4 to C6 polyol selected from the group consisting of pentaerythritol, trimethylol propane, neopentyl glycol, and mixtures thereof. In an embodiment, at least about 90% by weight of the C4 to C6 polyol used in preparation of the reaction product is pentaerythritol. In an embodiment, at least about 90% by weight of the C4 to C6 polyol used in preparation of the reaction product is trimethylol propane. In an embodiment, at least about 90% by weight of the C4 to C6 polyol used in preparation of the reaction product is neopentyl glycol.

The reaction product typically is made by heating an aqueous mixture of itaconic acid, the Liquid Polyol Monomers, and the C4 to C6 polyols to a temperature of from about 115° C. to about 250° C. In an embodiment, the mixture is heated to a temperature of from about 130° C. to about 240'C. In an embodiment, the mixture is heated to a temperature of from about 150° C. to about 230'C. In an embodiment, the temperature of the reaction vessel held at a constant temperature during the reaction. In an embodiment, the reaction vessel is held at a first low temperature for a portion of the reaction time, is increased to a second higher temperature for a later portion of the reaction time. In an embodiment, the first low temperature is below about 200'C and the second higher temperature is above about 200° C.

The mixture of may be heated under vacuum, at ambient pressures, or under pressure in a sealed reaction vessel.

The ingredients combined to form the reaction product may be charged to the reaction vessel in any suitable manner. In an embodiment, all of the ingredients are charged essentially simultaneously prior to or during heating. In an embodiment, the low viscosity ingredients are charged first to assure proper mixing, followed by higher viscosity ingredients. In an embodiment, the Liquid Polyol Monomers and polyols are charged in the desired molar ratios prior to addition of the itaconic acid.

In an embodiment of the present invention, the molar ratio of the combined alcohols (Liquid Polyol Monomers and C4 to C6 polyols) to itaconic acid is at least 2:1. In an embodiment of the present invention, the molar ratio of the combined alcohols (Liquid Polyol Monomers and C4 to C6 polyols) to itaconic acid is from 2:1 to about 5:1. In an embodiment of the present invention, the molar ratio of the combined alcohols (Liquid Polyol Monomers and C4 to C6 polyols) to itaconic acid is from 2:1 to about 4:1. In an embodiment of the present invention, the molar ratio of the combined alcohols (Liquid Polyol Monomers and C4 to C6 polyols) to itaconic acid is from 2:1 to about 3:1. In an embodiment of the present invention, the molar ratio of the combined alcohols (Liquid Polyol Monomers and C4 to C6 polyols) to itaconic acid is from 2:1 to about 2.5:1.

In each of the above listed embodiments of molar ratio of the combined alcohols to itaconic acid, the molar ratio of Liquid Polyol Monomers to C4 to C6 polyols may in an embodiment be from about 1:1 to about 30:1. In each of the above listed embodiments of molar ratio of the combined alcohols to itaconic acid, the molar ratio of Liquid Polyol Monomers to C4 to C6 polyols may in an embodiment be from about 2:1 to about 25:1. In each of the above listed embodiments of molar ratio of the combined alcohols to itaconic acid, the molar ratio of Liquid Polyol Monomers to C4 to C6 polyols may alternatively be from about 4:1 to about 20:1. In each of the above listed embodiments of molar ratio of the combined alcohols to itaconic acid, the molar ratio of Liquid Polyol Monomers to C4 to C6 polyols may alternatively be from about 4:1 to about 10:1.

In an embodiment, unreacted components are removed from the reaction product composition before formulation as an aqueous binder composition. In a preferred embodiment, unreacted components are not removed from the reaction product composition. While not being bound by theory, it is believed that unreacted Liquid Polyol Monomers and polyols that may be present in the reaction product composition may assist in compatibilizing the reaction product in the reaction product composition and/or the final binder composition to provide a stable formulation.

In an embodiment, the reaction product composition comprises at least a 70% yield of a reaction product that is a di-ester of itaconic acid with one Liquid Polyol Monomers and one C4 to C6 polyol. In an embodiment, the reaction product composition comprises at least a 75% yield or an 85% yield of a reaction product that is a di-ester of itaconic acid with one Liquid Polyol Monomers and one C4 to C6 polyol.

In an embodiment the amount of Liquid Polyol Monomers present in the reaction product composition is sufficiently low to provide an aqueous binder composition that does not produce visible smoke when heated to a temperature of 230° C.

In an embodiment, a small amount of water is added to the reaction product composition after preparation thereof form an aqueous binder concentrate. This concentrate is particularly suitable for storage and/or transport for later formulation into more dilute aqueous binder compositions. In an embodiment, the aqueous binder concentrate may itself be used without further dilution for applications such as a binder or an adhesive application.

In an embodiment, the solids content of the aqueous binder concentrate is from about 30 to about 90% by wt. In an embodiment, the solids content of the aqueous binder concentrate is from about 40 to 90%. In an embodiment, the solids content of the aqueous binder concentrate is from about 50 to 90%. For purposes of the present invention, "solids content" is defined as the content of all ingredients other than water, whether the ingredients are in solid or liquid form.

It has been discovered that the aqueous binder concentrate may have a longer shelf life by adjusting the pH of the aqueous binder concentrate to above about 6. In an embodiment, the pH of the aqueous binder concentrate is adjusted to from about 6 to 8, or from about 6.5 to about 7.5. In an embodiment, the pH of the aqueous binder concentrate is adjusted to provide a shelf life at 25° C. and 40% solids of greater than three months. In an embodiment, the pH of the aqueous binder concentrate is adjusted to provide a shelf life at 25° C. and 40% solids of greater than six months. For purposes of the present invention, shelf life is defined as the time that a composition continues to be flowable after having been stored at a given temperature without stirring.

The aqueous binder concentrate has a surprisingly low viscosity in view of the relatively high solids content, which provides benefit in material handling during transfer and under conditions of ultimate use. In an embodiment, the aqueous binder concentrate has a viscosity of from about 1 cs to about 1000 cs. In an embodiment, the aqueous binder concentrate has a viscosity of from about 1 cs to about 500 cs. In an embodiment, the aqueous binder concentrate has a viscosity of from about 1 cs to about 200 cs. In an embodiment, the aqueous binder concentrate has a viscosity of from about 1 cs to about 100 cs. In an embodiment, the aqueous binder concentrate has a viscosity of from about 1 cs to about 50 cs. In an embodiment, the aqueous binder concentrate has a viscosity of from about 1 cs to about 10 cs. In an embodiment, the aqueous binder concentrate has a viscosity of from about 1 cs to about 2 cs. Viscosity is measured by ASTM D-445 at 40° C.

Because the aqueous binder concentrate has such a low viscosity, the ultimate aqueous binder compositions may surprisingly be used at comparatively high solids content. This provides exceptional benefit because the aqueous binder compositions have relatively low water content. Specifically, water-based binder compositions require removal of water as part of the cure process. The present binder compositions advantageously may be formulated to have much less water content than conventional water-based binder systems, and therefore afford substantial savings in time and/or energy required to be put into the system to drive out the water.

An aqueous binder composition is formulated by mixing the reaction product (or aqueous binder concentrate is such is used as an intermediate composition, for example, for transport or storage) with water and such additional appropriate binder ingredients as desired. In an embodiment, the additional binder ingredients are added just prior to use of the binder. In an embodiment, the aqueous binder composition is provided as a kit having one part that is the binder component comprising reaction product and water, and at least one part that is an additive component comprising such additional appropriate binder ingredients as desired.

In an embodiment, the aqueous binder composition as applied in the final adhesive usage has a solids content of from about 10% to about 80% by weight, or from about 12% to about 35% by weight, or from about 15% to about 25% by weight.

In an embodiment, the aqueous binder composition as applied in the final adhesive usage has a pH of less than about 5, or from about 2.5 to about 4. It has surprisingly been found that while it is advantageous to store aqueous binder concentrate or the aqueous binder composition at a higher pH as noted above, it is further advantageous to adjust the pH of the aqueous binder concentrate or the aqueous binder composition just before use to a pH that is less than about 5 or from about 2.5 to about 4. Such compositions have surprisingly exhibited improved tensile strength over like compositions that are used at the higher pH.

In an embodiment, the aqueous binder composition as applied in the final usage has a viscosity of from about 1 cSt to about 200 cSt at 40° C. In an embodiment, the aqueous binder composition as applied in the final usage has a viscosity of from about 1 cSt to about 100 cSt at 40° C. In an embodiment, the aqueous binder composition as applied in the final usage has a viscosity of from about 1 cSt to about 50 cSt at 40° C. In an embodiment, the aqueous binder composition as applied in the final usage has a viscosity of from about 1 cSt to about 10 cSt at 40° C. In an embodiment, the aqueous binder composition as applied in the final usage has a viscosity of from about 1 cSt to about 2 cSt at 40° C.

In an embodiment, the binder composition further comprises an accelerant oligomer/polymer having a molecular weight of from about 520 to about 4900, wherein the accelerant oligomer/polymer is reactive with the vinyl functionality on the reaction product. In an embodiment, the accelerant oligomer/polymer is a pre-reacted itaconic acid-based oligomer/polymer having a molecular weight of from about 520 to about 4900. In an embodiment, the pre-reacted itaconic acid-based oligomer/polymer has a molecular weight of from about 520 to about 700.

In an embodiment, the accelerant oligomer/polymer is a poly(meth)acrylate that is reactive with the vinyl functionality on the reaction product and/or by esterification of the hydroxyls on the primary resin.

In an embodiment, the accelerant oligomer/polymer is present in an amount of from about 0.5 wt % to about 15 wt % of the composition based on solids content. In an embodiment, the accelerant oligomer/polymer is present in an amount of from about 1 wt % to about 10 wt % of the composition.

In an embodiment, the binder composition further comprises one or more coupling agents that are useful for enhancing compatibility of the binder with the fibers. In at least one exemplary embodiment, the coupling agent is a silane coupling agent. The coupling agent(s) may be present in the binder composition in an amount from about 0.0015% to about 0.75% by weight of the total composition, from about 0.005% to about 0.4% by weight, or from about 0.015% to about 0.08% by weight. Non-limiting examples of silane coupling agents that may be used in the binder composition may be characterized by the functional groups alkyl, aryl, amino, epoxy, vinyl, methacryloxy, ureido, isocyanato, and mercapto. In exemplary embodiments, the silane coupling agent(s) include silanes containing one or more nitrogen atoms that have one or more functional groups such as amine (primary, secondary, tertiary, and quaternary), amino, imino, amido, imido, ureido, or isocyanato. Specific, non-limiting examples of suitable silane coupling agents include, but are not limited to, aminosilanes (e.g., 3-aminopropyl-triethoxysilane and 3-aminopropyl-trihydroxysilane), epoxy trialkoxysilanes (e.g., 3-glycidoxypropyltrimethoxysilane and 3-glycidoxypropyltriethoxysilane), methyacryl trialkoxysilanes (e.g., 3-methacryloxypropyltrimethoxysilane and 3-methacryloxypropyltriethoxysilane), hydrocarbon trialkoxysilanes, amino trihydroxysilanes, epoxy trihydroxysilanes, methacryl trihydroxy silanes, and/or hydrocarbon trihydroxysilanes. In one or more exemplary embodiment, the silane is an aminosilane, such as γ-aminopropyltriethoxysilane.

Further exemplary coupling agents (including silane coupling agents) suitable for use in the binder composition are set forth below:

Acryl: 3-acryloxypropyltrimethoxysilane; 3-acryloxypropyltriethoxysilane; 3-acryloxypropylmethyldimethoxysilane; 3-acryloxypropylmethyldiethoxysilane; 3-methacryloxypropyltrimethoxysilane; 3-methacryloxypropyltriethoxysilane Amino: aminopropylmethyldimethoxysilane; aminopropyltriethoxysilane; aminopropyltrimethoxysilane/

EtOH; aminopropyltrimethoxysilane; N-(2-aminoethyl)-3-aminopropyltrimethoxysilane; N-(2-aminoethyl)-3-aminopropylmethyldimethoxysilane; (2-aminoethyl)-(2-aminoethyl) 3-aminopropyltrimethoxysilane; N-phenylaminopropyltrimethoxysilane Epoxy: 3-Glycidoxypropylmethyldiethoxysilane; 3-glycidoxypropylmethyldimethoxysilane; 3-glycidoxypropyltriethoxysilane; 2-(3,4-eoxycyclohexyl)ethylmethyldimethoxysilane; 2-(3,4-epoxycyclohexyl) ethylmethyldiethoxysilane; 2-(3,4-epoxycyclohexyl) ethyltrimethoxysilane; 2-(3,4-Epoxycyclohexyl) ethyltriethoxysilane Mercapto: 3-mercaptopropyltrimethoxysilane; 3-Mercaptopropyltriethoxysilane; 3-mercaptopropylmethyldimethoxysilane; 3-Mercaptopropylmethyldiethoxysilane Sulfide: bis[3-(triethoxysilyl)propyl]-tetrasulfide; bis[3-(triethoxysilyl)propyl]-disulfide Vinyl: vinyltrimethoxysilane; vinyltriethoxysilane; vinyl tris(2-methoxyethoxy)silane; vinyltrichlorosilane; trimethylvinylsilane Alkyl: methyltrimethoxysilane; methyltriethoxysilane; dimethyldimethoxysilane; dimethyldiethoxysilane; tetramethoxysilane; tetraethoxysilane; ethyltriethoxysilane; n-propyltrimethoxysilane; n-propyltriethoxysilane; isobutyltrimethoxysilane; hexyltrimethoxysilane; hexyltriethoxysilane; octyltrimethoxysilane; decyltrimethoxysilane; decyltriethoxysilane; octyltriethoxysilane; tert-butyldimethylchlorosilane; cyclohexylmethyldimethoxysilane; dicylohexyldimethoxysilane; cyclohexylethyldimethoxysilane; t-butylmethyldimethoxysilane Chloroalkyl: 3-chloropropyltriethoxysilane; 3-chloropropyltrimethoxysilane; 3-chloropropylmethyldimethoxysilane Perfluoro: decafluoro-1,1,2,2-tetrahydrodecyl)trimethoxysilane; ((heptadecafluoro-1,1,2,2-tetrahydrodecyl) trimethoxysilane Phenyl: phenyltrimethoxysilane; phenyltriethoxysilane; diphenyldiethoxysilane; diphenyldimethoxysilane; diphenyldichlorosilane Hydrolyzates of the silanes listed above Zirconates: zirconium acetylacetonate; zirconium methacrylate Titanates: tetra-methyl titanate; tetra-ethyl titanate; tetra-n-propyl titanate; tetra-isopropyl titanate; tetra-isobutyl titanate; tetra-sec-butyl titanate; tetra-tert-butyl titanate; mono n-butyl, trimethyl titanate; mono ethyl tricyclohexyl titanate; tetra-n-amyl titanate; tetra-n-hexyl titanate; tetra-cyclopentyl titanate; tetra-cyclohexyl titanate; tetra-n-decyl titanate; tetra n-dodecyl titanate; tetra (2-ethyl hexyl) titanate; tetra octylene glycol titanate ester, tetrapropylene glycol titanate ester; tetra benzyl titanate; tetra-p-chloro benzyl titanate; tetra 2-chloroethyl titanate; tetra 2-bromoethyl titanate; tetra 2-methoxyethyl titanate; tetra 2-ethoxyethyl titanate.

In an embodiment, the binder composition further comprises a dust suppression agent such as a mineral oil, modified vegetable oil, modified peanut oil, silicone, and the like. In an embodiment a dust suppression agent is present in the binder composition in an amount from about 0.1 to about 5% by glass weight.

In an embodiment, the binder composition further comprises conventional additives such as, but not limited to corrosion inhibitors, dyes, pigments, fillers, colorants, UV stabilizers, thermal stabilizers, anti-foaming agents, antioxidants, emulsifiers, preservatives (e.g., sodium benzoate), biocides, fungicides, and mixtures thereof. Other additives may be added to the binder composition for the improvement of process and product performance. Such additives include lubricants, wetting agents, surfactants, antistatic agents, and/or water repellent agents. Additives may be present in the binder composition from trace amounts (such as <about 0.1% by weight the binder composition) up to about 1.5% by weight of the total solids in the binder composition. In some exemplary embodiments, the additives are present in an amount from about 0.015% to about 0.75% by weight of the total binder composition, or from about 0.15% to about 0.6% by weight of the total binder composition, or from about 2.2% to about 0.5% by weight of the total binder composition.

In an embodiment, the aqueous binder may be characterized by the absence of formaldehyde.

In an embodiment, added moisture resistant agents are not needed for the binders of the present invention, because through selection of the balance of alcohol components in the formation of the reaction product, the binder formulation does not exhibit humectant properties.

In certain preferred aspects of the above embodiments, the aqueous binder composition contains less than 500 ppm chloride ions. In other preferred aspects, the aqueous binder contains less than 300 ppm, less than 200 ppm, less than 100 ppm, less than 70 ppm, or less than 50 ppm chloride ions. Reduced chloride ions concentrations may minimize corrosion concerns in binder compositions.

In an embodiment, a catalyst is added just before use as a binder in order to initiate the polymerization reaction of the vinyl functionalities present in the binder composition.

In an embodiment, the catalyst is selected from the group consisting of ferric ammonium sulfate, metal salts of persulfate, permanganate metal salts, t-butyl peroxide, hydrogen peroxide, benzoyl peroxide, or any free radical generators.

The catalyst is in an embodiment present at an amount of from about 0.1 to about 3 wt %, or from about 0.1 to about 0.3 wt % based on the weight of the reaction product and the (optional) pre-reacted itaconic acid-based oligomer/polymer at 40% solids content.

In an embodiment, the binder composition additionally comprises a difunctional crosslinker capable of reacting with the available hydroxyl functionalities present in the reaction product. Examples of suitable crosslinkers are diacid compounds. In an embodiment, the binder composition does not contain polyacid compounds having three or more acid functionalities.

In an embodiment, the binder composition may be prepared by dissolving or dispersing the catalyst in water to form a mixture. The reaction product and optional accelerant oligomer/polymer may be added to the binder composition, after which the coupling agent(s), dust suppression agent (e.g., mineral oil), and any desired additives may be added. The binder composition may be further diluted with water to obtain a desired amount of solids. If necessary, the pH of the mixture may be adjusted to the desired pH level with organic and inorganic acids and bases.

In an embodiment of the present invention, fibrous insulation products or non-woven mats are formed of matted inorganic fibers bonded together by a cured binder material. Examples of suitable inorganic fibers include glass fibers, wool glass fibers, and ceramic fibers. Optionally, other reinforcing fibers such as natural fibers and/or synthetic fibers such as polyester, polyethylene, polyethylene terephthalate, polypropylene, polyamide, aramid, and/or polyaramid fibers may be present in the insulation product in addition to the glass fibers. The term "natural fiber" as used in conjunction with the present invention refers to plant fibers extracted from any part of a plant, including, but not limited to, the stem, seeds, leaves, roots, or phloem. Examples of natural fibers suitable for use as the reinforcing fiber material include basalt, cotton, jute, bamboo, ramie, bagasse, hemp, coir, linen, kenaf, sisal, flax, henequen, and combinations thereof. Insulation products may be formed entirely of one type of fiber, or they may be formed of a combination of types of fibers. For example, the insulation product may be formed of combinations of various types of glass fibers or various combinations of different inorganic fibers and/or natural fibers depending on the desired application for the insulation.

Products made using the present binder compositions may advantageously exhibit high fluff characteristics, excellent R values and a light color, which indicates absence of corrosive ingredients. A light color additionally allows the use of dyes, pigments, or other colorants to yield a variety of colors for the insulation or nonwoven mat product.

Insulation and non-woven mats may be prepared using the present aqueous binder compositions by conventional non-woven processing techniques, including dry laid and wet laid processes.

In an embodiment, the manufacture of glass fiber insulation may be carried out in a continuous process by fiberizing molten glass, immediately forming a fibrous glass batt on a moving conveyor, and curing the binder on the fibrous glass insulation batt to form an insulation blanket. In an embodiment, the curing step comprises passing the insulation blanket through an oven.

In an embodiment of the present invention, the binder composition may be used to form a non-woven chopped strand mat. In particular, binder is added during the formation of the chopped strand mat in a wet-laid mat processing line.

Aqueous binder compositions of the present invention can be useful for composite reinforcements, such as chopped strands, for use in thermoplastics, thermosets, and roofing applications. In addition, the inventive binders may be used in both single and multi-end rovings.

In an embodiment, the aqueous binder compositions may be used in formation of sand molds, for example in casting operations. Use of the aqueous binder compositions is silaceous molds is specifically contemplated. Surprisingly the present aqueous binder compositions may be effective in mold formation at low solids content, e.g. at binder solids content of 0.5 to 2 parts per 100 of the sand material.

In an embodiment, the aqueous binder compositions may be used as a dust control agent for stabilizing dust on surfaces such as roads, mining operations and the like. In particular, the aqueous binder compositions may be used as a dust control agent for stabilizing dust generated from silaceous materials.

In an embodiment, the aqueous binder compositions may be used in fiberboard construction and other such applications where fibers and/or particles are adhered to surfaces or to other fibers and/or particles.

EXAMPLES

Representative embodiments of the present invention will now be described with reference to the following examples that illustrate the principles and practice of the present invention.

Procedures

A. Preparation of Fiberglass Mat.

The aqueous binder composition was applied to a glass fiber sheet using the following methodology:

1. Cut the glass-fiber sheet using a paper-strip sample cutter (width 2.5 cm, length ~19 cm).
2. Weigh the glass-fiber sheet samples.
3. Soak a pre-weighed sheet in a 80 g of binder solution in a cooking pan (22 cm×32 cm, about 20-30 degree tilted) with help of a roller to remove trapped air on the fiber strip. % Solid of binder solution varies from 15% to 30% to adjust pick-up rate.
4. Move the soaked sheet out of the solution on a pan. Then, apply light pressure with a roller on the wet fiber-sheet to remove excess binder solution from the sample. Do not apply the force (weight) on the sheet when a roller was used. Use roller's weight only to squeeze out the excess binder from a sheet.
5. Place the sheet sample on 2 blotter papers stacked.
6. Place 2 other blotter papers on the sample to cover.
7. Roll a roller (28 lb) on the blotter paper 2 round trips to absorb excess binder solution out from a glass-fiber sheet. A roller and blotter paper are from a hand-sheet preparation method from TAPPI.
8. Dry the dewatered sample sheet using a speedy hand-sheet dryer set at for 20 min.
9. Further curing is done in a convection oven set at 120° C.
10. Keep the dried samples in a desiccator to weigh the sample with a binder.
11. Calculate the amount of binder on a sample sheet using the following equation:

$$\% \text{ Wt. of a Binder on a sample}=100*\{(\text{Wt of sheet with a binder})-(\text{wt. of sheet})\}/(\text{Wt. of Sheet})$$

B. Tensile Evaluation

The tensile properties of formed mats were evaluated using the following methodology:

1. A fiberglass filter paper is placed in a Buchner funnel with vacuum being pulled from the funnel stem. While the vacuum is being pulled, a known volume of aqueous binder composition is poured onto the filter paper. The vacuum is continued for a fixed period of time after the aqueous binder composition has been deposited. The vacuum is then turned off and the filter paper carefully removed from the funnel. The filter paper is then cured at about 200° C. for 120 seconds.
2. The thus prepared sheets are cut in half to provide two sample sheets for each material. Data from these two samples are averaged. The sample sheets are equilibrated at the testing room environment for 24-48 hours before test.
3. Measurements of tensile strength and extensional property are taken of the samples and an additional sample of untreated filter paper (to establish a control for tensile strength). Measurements are taken using an Instron tensile tester under uniform test parameters for cross-comparability of sample data.
4. The observed tensile measurement values are normalized to account for different coating weights as follows:

Fiberglass that has been coated with binder and dust control oil and fully cured is tested for binder weight. A known mass of cured fiberglass is placed in a high temperature oven at greater than 500 C until a constant weight is measured. The glass weight after burn off is subtracted from the initial coated glass weight. The result is the weight of resin and oil that was on the glass. This number is then divided by the initial coated glass weight to get a normalized coating weight per glass weight, which is known as Loss On Ignition, or "LOI."

Comparative Example 1—Glycerol and Itaconic Acid 500 g USP Glycerol and 250 g itaconic acid were added to a 1000 ml reactor. The reactor was purged with nitrogen for less than a half hour prior to heating and continued through the entirety of the reaction. The reactor was heated to 230° Celsius. The temperature remained at 230° Celsius until the acid value reached less than 5 mg potassium hydroxide per gram sample. The reactor was cooled to less than 100° Celsius and diluted with water to 40 weight percent solids to form an aqueous binder composition.

Fiberglass mats are prepared using the procedure A described above.

The aqueous binder composition of Comparative Example 1 was found to exhibit slow cure times due to humectant effect of the glycerol. Additionally, heavy smoke was generated by this composition during heating to cure on the fiberglass to form the mat. Therefore, the composition of this Comparative Example was not suitable for use as a binder composition.

Comparative Example 2—Glycerol and Itaconic Acid—Low Relative Amount of Glycerol 169.56 g USP Glycerol and 130.43 g itaconic acid was added to a 500 ml reactor to create a mole ratio of 1.85 moles USP glycerol to 1.00 moles Itaconic acid. The reactor was purged with nitrogen for less than a half hour prior to heating and continued through the entirety of the reaction. The reactor was heated to 230 degrees Celsius. The temperature remained at 230 degrees Celsius. The product solidified in the reactor two hours and forty minutes into the reaction, and so the composition of this Comparative Example was not suitable for use as a binder composition.

Example 1—Glycerol, Penterythritol and Itaconic Acid 1876 g USP Glycerol, 350 g pentaerythritol, and 1274 g itaconic acid were added to a 5000 ml reactor. The reactor was purged with nitrogen for less than a half hour prior to heating and continued through the entirety of the reaction. The reactor was heated to 160° Celsius. The temperature remained at 160° Celsius until the acid value reached 50 mg potassium hydroxide per gram sample. Once this acid value was achieved, the reactor was heated to 180° Celsius and remained there until an acid value less than 5 mg potassium hydroxide per gram sample was achieved. The reactor was cooled to less than 100 degrees Celsius and diluted with water to 40 weight percent solids. The pH of this composition was about 3.0-3.1.

The aqueous binder composition was applied to a glass fiber sheet using the methodology described above Fiberglass mats were prepared and Tensile evaluations were performed using the procedures A and B described above.

The thus prepared aqueous binder composition was found to exhibit a good tensile strength, high ramp height and low odor. Additionally, the hand feel of the mat is soft as compared to phenol-formaldehyde (PF) binders.

Example 2—Glycerol, Neopentyl Glycol, Trimethylolpropane, and Itaconic Acid 402 g USP Glycerol, 28.65 g neopentyl glycol, 36.9 g trimethylolpropane, and 273 g itaconic acid was added to a 1000 ml flask. The reactor was purged with nitrogen for less than a half hour prior to heating and continued through the entirety of the reaction. The reactor was heated at temperatures up to 200 degrees Celsius. The temperature remained at 200 degrees Celsius until the acid value reached less than 5 mg potassium hydroxide per gram sample. The reactor was cooled to less than 100 degrees Celsius and diluted with water to 40 weight percent solids.

Comparative Example 3—High Relative Amount of Pentaerythritol

A reaction was carried out using 44.6% glycerol/36.45 itaconic acid/19.0%/pentaerythritol as reactants under the same reaction conditions as in Example 2 above. This reaction failed, as the product became solid in the reactor at 200° C.

Comparative Example 4—High Relative Amount of Pentaerythritol

A series of reactions were carried out with decreasing amounts of pentaerythritol under the same reaction conditions as in Comparative Example 3. All went solid. The maximum amount of pentaerythritol was found to be 11.0%. At 11.0% pentaerythritol, the resin did spontaneously cure after several days of storage in a clear glass bottle not under nitrogen blanket, and so was also considered a failure.

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. Examples of such limitations include preparing the sample in a wet versus a dry environment, different instruments, variations in sample height, and differing requirements in signal-to-noise ratios. For example, "about" can mean greater or lesser than the value or range of values stated by 1/10 of the stated values, but is not intended to limit any value or range of values to only this broader definition. For instance, a concentration value of about 30% means a concentration between 27% and 33%. Each value or range of values preceded by the term "about" is also intended to encompass the embodiment of the stated absolute value or range of values.

Throughout this specification and claims, unless the context requires otherwise, the word "comprise", and variations such as "comprises" and "comprising", will be understood to imply the inclusion of a stated integer or step or group of integers or steps but not the exclusion of any other integer or step or group of integer or step. When used herein "consisting of" excludes any element, step, or ingredient not specified in the claim element. When used herein, "consisting essentially of" does not exclude materials or steps that do not materially affect the basic and novel characteristics of the claim. In the present disclosure of various embodiments, any of the terms "comprising", "consisting essentially of" and "consisting of" used in the description of an embodiment may be replaced with either of the other two terms.

All patents, patent applications (including provisional applications), and publications cited herein are incorporated by reference as if individually incorporated for all purposes.

Unless otherwise indicated, all parts and percentages are by weight and all molecular weights are weight average molecular weights. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A fibrous insulation product comprising:
   a plurality of randomly oriented fibers; and
   a binder composition comprising water and a reaction product of:
   a) one or more Liquid Polyol Monomers;
   b) itaconic acid, or its salt or anhydride; and
   c) a C4 to C6 polyol selected from the group consisting of pentaerythritol, trimethylol propane, neopentyl glycol, and mixtures thereof;
   wherein the molar ratio of the combined Liquid Polyol Monomers and C4 to C6 polyols to itaconic acid is at least 2:1, and wherein the molar ratio of Liquid Polyol Monomers to C4 to C6 polyols from about 1:1 to about 30:1.

2. The fibrous insultation product of claim 1, wherein such binder composition comprises a molar ratio of the combined Liquid Polyol Monomers and C4 to C6 polyols to itaconic acid is from 2:1 to about 5:1, wherein the molar ratio of Liquid Polyol Monomers to C4 to C6 polyols is from about 1:1 to about 30:1.

3. The fibrous insultation product of claim 1, wherein such Liquid Polyol Monomers have a melting point below 23° C. and wherein such binder composition comprises a molar ratio of the combined Liquid Polyol Monomers and C4 to C6 polyols to itaconic acid is from 2:1 to about 4:1, wherein the molar ratio of Liquid Polyol Monomers to C4 to C6 polyols is from about 1:1 to about 30:1.

4. The fibrous insultation product of claim 1, wherein such binder composition comprises a molar ratio of the combined Liquid Polyol Monomers and C4 to C6 polyols to itaconic acid is from 2:1 to about 3:1, wherein the molar ratio of Liquid Polyol Monomers to C4 to C6 polyols is from about 1:1 to about 30:1.

5. The fibrous insultation product of claim 1, wherein such binder composition comprises a molar ratio of Liquid Polyol Monomers to C4 to C6 polyols is from about 2:1 to about 25:1.

6. The fibrous insultation product of claim 1, wherein such binder composition comprises a molar ratio of Liquid Polyol Monomers to C4 to C6 polyols is from about 4:1 to about 20:1.

7. The fibrous insultation product of claim 1, wherein such binder composition comprises a molar ratio of Liquid Polyol Monomers to C4 to C6 polyols is from about 4:1 to about 10:1.

8. The fibrous insulation product of claim 1, wherein at least about 90% by weight of the Liquid Polyol Monomers used in preparation of the reaction product is glycerol.

9. The fibrous insultation product of claim 1, wherein at least about 90% by weight of the Liquid Polyol Monomers used in preparation of the reaction product is propylene glycol.

10. The fibrous insultation product of claim 1, wherein at least about 90% by weight of the C4 to C6 polyol used in preparation of the reaction product is pentaerythritol.

11. The fibrous insultation product of claim 1, wherein at least about 90% by weight of the C4 to C6 polyol used in preparation of the reaction product is trimethylol propane.

12. The fibrous insultation product of claim 1, wherein at least about 90% by weight of the C4 to C6 polyol used in preparation of the reaction product is neopentyl glycol.

13. The fibrous insultation product of claim 1, wherein the aqueous binder composition comprises unreacted glycerol.

14. The fibrous insultation product of claim 1, wherein the aqueous binder composition has a solids content of from about 30 to 80% by weight.

15. The fibrous insultation product of claim 1, wherein the aqueous binder composition further comprises an accelerant oligomer/polymer that is reactive with a vinyl functionality on the reaction product.

16. The fibrous insultation product of claim 1, wherein the accelerant oligomer/polymer has a molecular weight of from about 520 to about 4900.

17. The fibrous insultation product of claim 1, wherein the accelerant oligomer/polymer is present in an amount of from about 0.5 wt % to about 15 wt % of the composition based on solids content.

18. The fibrous insultation product of claim 1, wherein the aqueous binder composition contains less than 500 ppm chloride ions.

19. The fibrous insultation product of claim 1, wherein the aqueous binder composition is adjusted in pH during or after formulation by addition of base in an amount sufficient to provide a pH of from about 5 to 9.

20. The fibrous insultation product of claim 1, wherein the aqueous binder composition comprises a catalyst capable of initiating a polymerization reaction of vinyl functionalities present in the binder composition.

21. The fibrous insultation product of claim 1, wherein the catalyst is ferric ammonium sulfate.

* * * * *